United States Patent [19]

Bakalyar et al.

[11] 4,133,767

[45] Jan. 9, 1979

[54] CHROMATOGRAPHIC APPARATUS AND METHOD

[75] Inventors: Stephen R. Bakalyar, Berkeley; Ronald E. Honganen, Campbell, both of Calif.

[73] Assignee: Spectra-Physics, Inc., Mountain View, Calif.

[21] Appl. No.: 806,457

[22] Filed: Jun. 14, 1977

[51] Int. Cl.² ............................................. B01D 15/03
[52] U.S. Cl. ..................................... 210/31 C; 55/47; 55/53
[58] Field of Search ................ 210/31 C, 198 C, 101; 55/53, 47, 198

[56] References Cited

U.S. PATENT DOCUMENTS

| 2,511,833 | 6/1950 | Beckel et al. | 55/53 |
| 3,926,559 | 12/1975 | Stevens | 210/31 C |

Primary Examiner—John Adee
Attorney, Agent, or Firm—Flehr, Hohbach, Test, Albritton & Herbert

[57] ABSTRACT

Apparatus and method for liquid chromatography applicable to systems employing more than one solvent for the carrier. The forming of bubbles in the pumping means employed is prevented by special pretreatment of at least one solvent of the carrier, the pretreatment involving sparging of the solvent with inert gas.

9 Claims, 2 Drawing Figures

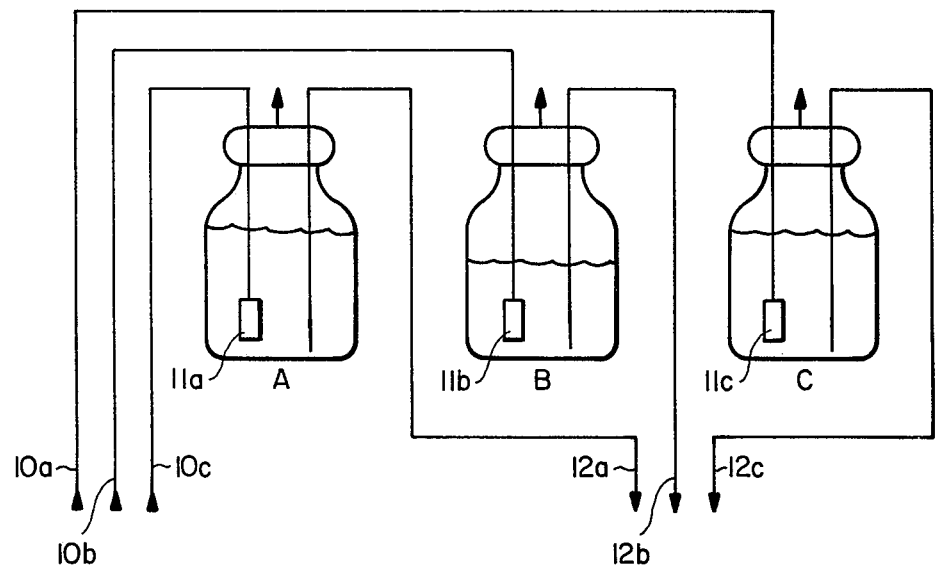
FIG_1
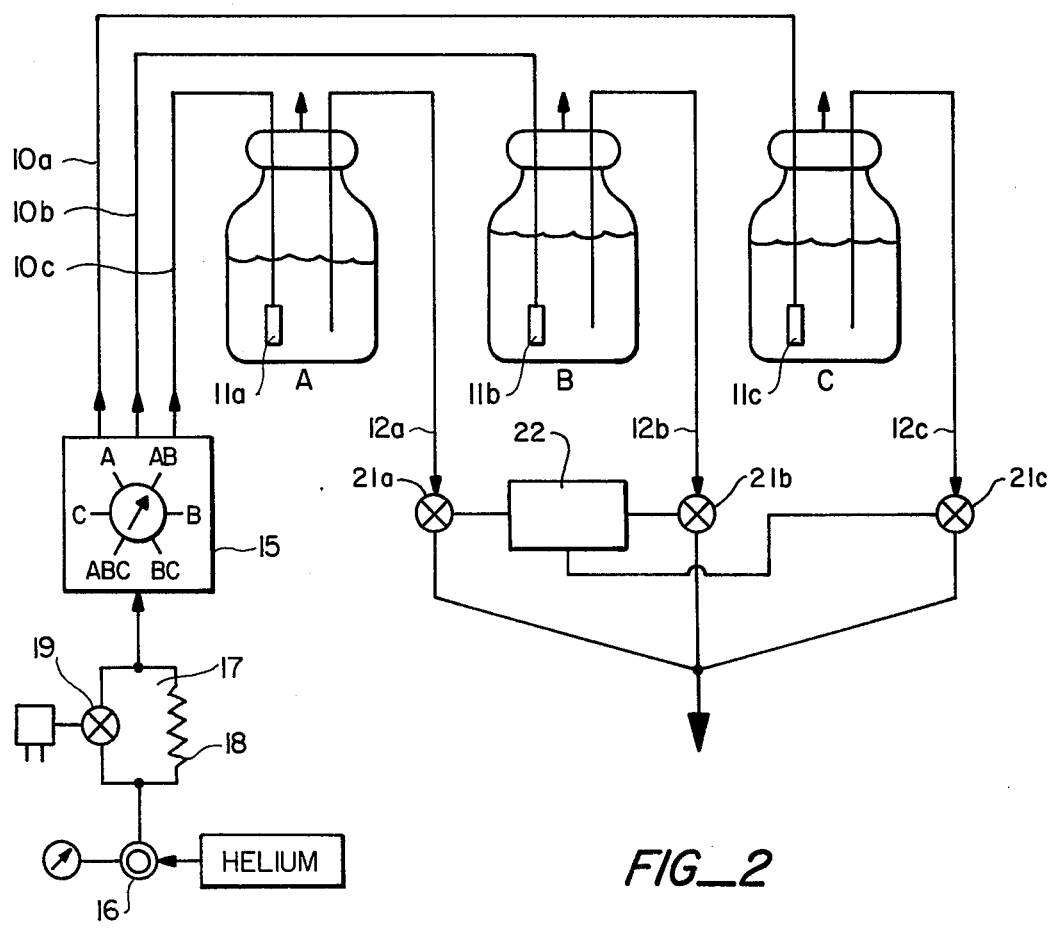
FIG_2

CHROMATOGRAPHIC APPARATUS AND METHOD

BACKGROUND OF THE INVENTION

This invention pertains generally to liquid chromatography and more particularly to apparatus and methods for pretreating the solvents employed.

Liquid chromatographic systems generally employ a carrier liquid solvent or solvent mixture which is delivered, often at high pressure, to a column. The column may be of the type that is packed with stationary phase particles, or may be an open tube whose inside walls are coated with stationary phase material (i.e., so called "capillary columns"). The material to be analyzed is injected into the flow of the liquid carrier as it passes to the column. The solvents employed may be non-polar, polar or of intermediate polar properties. The particular solvent or solvents used to prepare the carrier are selected according to the characteristics of the material to be analyzed, the nature of the column, and the overall objectives of the analysis. In instances where the presence of dissolved gases, such as air, is objectionable, it has been the practice to effect removal of substantially all of the gases from the solvent by heating to boiling temperature, by subjecting the solvent to a partial vacuum, by ultrasonics, or combinations of such treatments. The simpler chromatographic systems employ a pump of the positive displacement type, which delivers the carrier to the column at pressures of a few p.s.i. to 7000 p.s.i. or higher, depending on the type of column used and the flow rate employed. A typical pressure range is from 500 to 5000 p.s.i. Such systems may employ a carrier comprising a single solvent, or a binary or tertiary solvent mixture in an isocratic mode (the solvent composition constant) or a gradient mode (the solvent composition programmed with time). The latter systems may employ two or more pumps delivering separate solvents to a mixer, with the solvent mixture (i.e. carrier) then being delivered to the column. Another gradient system makes use of relatively low pressure metering pumps or proportioning valves which deliver solutions in the proportions desired to a manifold and/or mixer, and from thence to the inlet of a single high pressure positive displacement pump which delivers the solvent mixture to the column. In both instances the presence of bubbles in the solvent or solvent mixtures may cause difficulties such as errors in the flow rates from the pumping means employed and errors in the composition of the carrier. Both flow and composition errors degrade chromatographic performance in terms of retention time precision, peak area precision and detector noise level. Particularly with respect to gradient systems of the type which employ a single high pressure positive displacement pump which delivers the carrier at high pressure directly to the column, bubbles tend to form on the way into or in the high pressure pump, due to gases such as air present in one or more of the solvents supplied to the manifold or mixing chamber, which is at relatively low pressure. Such bubbles cause excessive compliance in the high pressure pump chamber, thus causing increased flow rate errors and pulsation. Prior methods of treating the solvents to eliminate dissolved air are subject to certain disadvantages when applied to gradient systems. The hardware required for such pretreatment is relatively elaborate and cumbersome in operation and does not maintain a steady state degassed condition. For example, after a partial vacuum is applied and then released (it is not desirable to maintain a vacuum on the solvent during pumping), the gas concentration of various gases in the solvent, usually the air gases, starts to increase and in time reaches saturation level. This increase in gas concentration not only increases the probability of bubble formation, but in addition causes other undesirable results. Among these are the following: The presence of oxygen in the solvent can cause oxidation and degradation of certain samples, columns, plumbing connections and solvents. For example, tetrahydrofuron solvent forms peroxides in the presence of oxygen, and these cause absorbance of ultraviolet (UV) light, resulting in drifting baselines when UV photometric detectors are used. Oxygen itself can cause detecting drift due to its own UV absorbancy, and to its ability to quench fluorescence (in the case of fluorescent detectors). Quenching also results in nonreproducible detector response, and therefore to poor quantitative accuracy in chromatographic analysis. Oxygen can also cause a high background current, drift and noise in certain detectors, such as electrochemical detectors and electron capture detectors. The presence of carbon dioxide in the solvent can cause the pH value (acidity) of the solvent to change. This in turn affects the retention time of some eluted peaks and changes their UV absorption characteristics. The result is poor quantitative analytical precision. Also, the prior methods do not permit uninterrupted chromatography, and may not maintain steady state gas concentrations.

OBJECTS OF THE INVENTION AND SUMMARY

In general it is an object of the invention to provide an improved apparatus and method for preventing the formation of bubbles in the composition forming and/or pumping means employed in multiple solvent systems (isocratic and gradient) used in liquid chromatography.

Another object is to provide a method for the pretreatment of solvents used in multiple solvent chromatography which effectively removes dissolved gases such as the components of air by a relatively simple procedure, and which prevents reabsorption of such gases into the solvent while the solvent is being pumped.

Another object is to avoid use of prior solvent pretreatment methods and to carry out pretreatment in a simple effective manner which facilitates and simplifies the hardware required and which produces rapid degassing that is constantly maintained.

In general, the present invention is applicable to both isocratic and gradient elution chromatography systems having pumping means for delivering a multi-solvent liquid carrier to a packed column, and where at least one of the solvents of the carrier contains an objectionable amount of dissolved air gases. The improvement consists in sparging at least the solvent having an objectionable amount of absorbed air gases before it is supplied to the pumping means, with a gas that is inert to the solvent and which has low solubility therein. The sparging is continued for a period of time sufficient to substantially eliminate air from the solvent and to saturate the solvent with the sparging gas. Also, preferably the sparging is carried out over a time period sufficient to produce an atmosphere comprising only the inert sparging gas in the space overlying the surface of the solvent, thus preventing reabsorption of oxygen, carbon dioxide or other gases into the solvent before and during the time it is supplied to the pumping means. When two or more solvents differing in polarity are used in the system and it is desired to remove dissolved gases from both or all of them, they are separately sparged and mixed to form the carrier. When one of the solvents is relatively polar (e.g., water) it may be mixed with one or more solvents of relatively less polarity (e.g., acetonitrile) that have been sparged. The preferred sparging gas is helium.

Additional objects and features of the invention will appear from the following description in which the preferred embodiment has been set forth in detail in conjunction with the accompanying drawing.

BRIEF DESCRIPTION OF THE DRAWING

FIG. 1 is a diagram schematically showing simple equipment for carrying out the invention.

FIG. 2 is another diagram showing more elaborate equipment.

DESCRIPTION OF THE PREFERRED EMBODIMENTS

As is well known, gases contained in a gas mixture, such as air, are independent in that one gas behaves in the presence of one or more other gases the same as if the other gases were not present. Also the different gases of such a gas mixture have different solubilities in a given solvent, and the different solvents have different solubility properties toward a given gas. In addition, the solubility properties of solvent mixtures such as are used in chromatography are not linearly related to the properties of the individual solvents. The present invention is predicated upon the discovery that in liquid chromatography sparging of solvents provides an effective and simple way to purge the solvent of air, provided the sparging gas is one that is relatively inert to the solvent, and that its solubility in the solvent is relatively low.

In practicing the invention, sparging is carried out in vessels containing the solvents, with the space overlying each solvent being enclosed except for a vent. Sparging is carried out by dispersing the inert gas into the lower portion of the vessel, which serves to effect sufficient agitation to produce a large gas-liquid interfacial area. During sparging the solvent is rapidly purged of absorbed air, and as sparging approaches completion the atmosphere overlying the solvent is likewise purged of air, whereby at the end of the sparging period the atmosphere overlying the solvent is essentially devoid of all gases except the sparging gas. Also at the end of an effective sparging period, the concentration of dissolved sparging gas in the solvent is at saturation and no other absorbed gases are present.

Helium has been found to be effective as a sparging gas for all of the solvents commonly used in liquid chromatography. Helium is completely inert to such solvents, and likewise it has relatively low solubility which varies for different solvents. In contrast, many of the gases of air, as for example, nitrogen, oxygen and carbon dioxide, have relatively high solubility in solvents. Thus solvent which contains a concentrate of dissolved air to the point of saturation has a relatively high content of such gases, compared to its content of helium after being sparged to saturation.

The equipment employed for carrying out the invention is relatively simple, but may vary in detail depending upon the character of the chromatographic equipment. The simplified equipment shown in FIG. 1 consists of three vessels A, B and C which contain separate solvents. Lines 10a, 10b and 10c are for introducing sparge gas, and they connect with gas dispersion means 11a, 11b and 11c, such as suitable microfilters. Lines 12a, 12b and 12c are for removing the solvents after purging and for supplying the same to the chromatography system. A vent to atmosphere connects with the space in the upper part of each vessel, as indicated. Suitable valve means can be associated with the lines 10a, 10b and 10c to enable purging gas to be supplied selectively to any one or more of the vessels A, B and C. Also lines 12a, 12b and 12c may deliver the purged solvents to means which mixes two or more of the solvents in predetermined ratios according to a preselected composition or programmed gradient. Assuming that it is desired to produce a mixture of solvents contained in the vessels B and C, helium gas is supplied by lines 10b and 10c to carry out sparging simultaneously in both vessels for a period of time sufficient to substantially complete removal of air from the solvents and to saturate the solvents with helium and to produce an atmosphere consisting only of helium in the spaces above the solvents. The solvents may be at ambient room temperature at the time of sparging, although in some instances it may be desirable to carry out sparging of one or more of the solvents at a somewhat higher temperature level, as for example, from 75 to 200° F. but well below the boiling point of the solvent.

Different ways in which the invention can be practiced are as follows. Assuming use of two solvents, they can both be sparged with helium. In this event, the formation of bubbles is eliminated, and in addition the unwanted gases such as oxygen, carbon dioxide, etc., are eliminated. When the two solvents differ substantially in polarity, the less polar solvent can be sparged with helium, without sparging the more polar solvent, thus permitting the latter to retain absorbed air. For example, with the solvent pair, water and acetonitrile, the less polar acetonitrile alone is sparged with helium and this is found to be sufficient to eliminate formation of bubbles upon mixing of the two solvents. However, the benefit of eliminating unwanted gases such as oxygen from the mixture is not obtained.

In some instances, two different gases may be used for sparging, each gas being directed toward its respective solvent. One of the gases is helium and it is sparged into the less polar of the two solvents. The other gas can be one like nitrogen which does not react with the solvent. It is preferable that the second gas have as low a solubility as possible in the solvent. For instance, in the solvent pair water and acetonitrile, the acetonitrile is sparged with helium, and the water with nitrogen. This method results in eliminating the bubble problem, and in addition eliminates all unwanted gases such as oxygen and carbon dioxide. It has the added benefit of conserving the use of helium, which is sometimes a relatively unavailable gas.

With regard to the above three modes of practicing the invention, it should be noted that in general the lower the polarity of a solvent, the higher is its capacity for absorbing the gases of air. However, all solvents have a relatively low capacity for helium. When a relatively nonpolar solvent is sparged with helium then, at the time of mixing of the sparged solvent with a more polar solvent which has not been sparged with any gas and which contains dissolved air, the resulting concentration in the polar solvent mixture is reduced well below saturation, and under such conditions it has been found that bubbles are not formed in the pumping equipment.

Solvent polarity, as this term is used in the foregoing description, is a relative property. It means that property of the solvent which chemists commonly refer to as describing its relative hydrophilicity or relative hydrophobicity. Polarity is a relative property. Thus water is said to be more polar than methanol, which in turn is more polar than hexane. A common measure of polarity is the Hildebrand solubility parameter. The Hildebrand solubility parameter of a few typical solvents are listed as follows:

Water: 21
Methyanol: 13
Acetonitrile: 12
Benzene: 9
Hexane: 7

Tests of the method have shown that the amount of helium required is not excessive, and that effective purging can be carried out over a relatively short period of time. Thus it has been found that when a vessel contains 1 liter of a solvent like methanol, it can be effectively purged by sparging with helium for a period of 5 minutes, with flow of the sparging gas at the rate of 1 liter per minute. Assuming that the solvent is saturated with air gases at the commencement of the purging period, the amount of air gases present is reduced to less than 0.01% of the saturation concentration. The amount of dissolved helium with which the solvent is saturated at the end of the sparging cycle is of the order of 0.03 cc per ml of methanol at ambient temperature and atmospheric pressure.

FIG. 2 illustrates somewhat more elaborate equipment. The vessels A, B and C are the same as in FIG. 1, but the lines 10a, 10b and 10c connect to a distribution valve 15. Helium is supplied from a source under pressure through a pressure reducing regulating valve 16 and the flow controlling means 17. Means 17 may consist of a flow restrictor 18, and a solenoid operated valve 19 shunted across the restrictor 18. The restrictor may be an extended length of small diameter tubing. When the solenoid valve 19 is open helium is supplied directly from the pressure reducer 16 through the distribution valve 15 to the selected ones of the vessels. As indicated, the valve 15 can be set in any one of the various positions to distribute the helium as desired. When the solenoid valve 19 is closed, helium gas is supplied at a relatively slow rate to the selected vessels, thereby ensuring maintenance of the sparged solvents in degassed condition during storage intervals and while the solvents are supplied to the mixing and pumping means. Lines 12a, 12b and 12c in this instance are shown connected to flow proportioning means 21a, 21b and 21c (e.g., proportioning valves or pumps) which are controlled by programming means 22 and which deliver the solvents to the common line 23.

To summarize, the present invention provides a relatively simple and effective method for elimination of dissolved air from solvents in multisolvent chromatographic systems (isocratic and gradient). It is deemed to be particularly beneficial in systems employing gradient elution chromatography. Assuming that the system makes use of a single high pressure pump which delivers the solvent mixture at realtively high pressure to a column, application of the method to one or more of the solvents being prepared for the mixture can be carried out with a minimum amount of hardware and with relatively simple operations being required of the operator. The degassing is reliable and effective in preventing formation of bubbles in the high pressure pump. Elimination of air gases such as oxygen and carbon dioxide from the sparged solvents makes for less oxidation of the column packing, and less corrosion of the hardware with which the solvent comes into contact. Also elimination of air gases from the solvents and the avoidance of high temperatures provides an element of safety. Gas concentration in the liquid carrier is maintained in a steady state during the time the carrier is supplied to the column. The character of the method is such that it permits uninterrupted chromatography. In general, the use of the method greatly simplifies the problems involved in the design and construction of gradient chromatography systems, and provides improved chromatographic performance, having reference to precision, accuracy and sensitivity.

As previously indicated, helium is preferred as a sparging gas because of its low solubility in the solvents generally used. As previously explained, in some instances nitrogen gas can be used, although its solubility is substantially higher than helium. Also both nitrogen and helium can be used on separate solvents. For examle, a relatively non-polar solvent in vessel A can be sparged with helium and a relatively polar solvent in vessel B can be sparged with nitrogen.

Examples of the invention are as follows:

EXAMPLE 1

In this example one solvent is relatively polar, namely water, and the second solvent is relatively nonpolar, namely methanol. One liter quantities of each solvent were placed in separate vessels and each sample sparged with helium at the rate of 1 liter of gas per minute, for a period of 5 minutes. Thereafter the flow of sparged gas was continued at a relatively low rate, namely at a rate of 10 ml per minute. The two sparged solvents were then employed to form the liquid carrier in a low pressure one pump chromatography system. It was observed that the carrier was free of bubble formation and that there was no evidence of absorbed air gases such as oxygen and carbon dioxide.

EXAMPLE 2

A relatively polar solvent, namely water, was employed together with a relatively less polar solvent, namely acetonitrile. Sparging was carried out in the same manner as in Example 1. Again it was noted that gas bubble problems had been eliminated and there was no evidence of contained air gases.

EXAMPLE 3

A relatively polar solvent, namely water, was used together with a less polar solvent, namely methanol. The water was sparged with nitrogen gas and the methanol sparged with helium. The amount of gas employed and the sparging times were substantially the same as in Example 1. It was noted that when the two sparged solvents were mixed and supplied to the pumping means of a one pump chromatography system no bubbles were formed, and there was no evidence of air gases in the carrier.

EXAMPLE 4

A relatively nonpolar solvent, namely heptane, was used together with two other solvents, namely methylene chloride and methanol. The ratio of solvents in the carrier mixture was 60:35:5 (heptane, methylene chloride; and methanol). Sparging was carried out on each sample in the manner described in Example 1. Again no evidence of gas bubbles existed in the liquid carrier resulting from the mixing of the sparged solvents, and there was no evidence of absorbed air gases in the carrier.

What is claimed is:

1. In multi-solvent chromatography systems having pumping means for delivering a liquid carrier to a column, the improvement comprising sparging at least one of the solvents before it is supplied to the pumping means with a gas that is inert to the solvent and which has low solubility in the solvent, the sparging being continued for a period of time sufficient to substantially eliminate gases of air from the same and to saturate the solvent with the sparging gas.

2. A method as in claim 1 in which the sparging gas is helium.

3. A method as in claim 1 in which the one solvent is sparged while in a vessel having a generally enclosed space overlying the surface of the solvent, the sparging serving to provide an atmosphere of only the sparging gas in said space.

4. A method as in claim 1 in which at least two solvents are sparged and the sparged solvents used to form the liquid carrier.

5. A method as in claim 1 in which at least two solvents differing in polarity are supplied to the system and mixed therein to form a carrier, and in which only the less polar of said solvents is sparged.

6. A method as in claim 5 in which both of said solvents are separately sparged.

7. A method as in claim 1 in which two solvents are supplied to the system and mixed therein to form a carrier, one of the solvents being of lower polarity than the other, sparging the one solvent with helium, sparging the other solvent with an inert gas which has low solubility in the solvent, and then mixing the sparged solvents and supplying said mixture as a carrier to the pumping means.

8. In multi-solvent chromatography systems having pumping means for delivering a liquid carrier to a column, the liquid carrier being a mixture of at least two solvents, at least one of which has an objectionable amount of absorbed air gases, the improvement comprising sparging said one solvent before it is mixed with the other solvent, the sparging being carried out by use of a gas that is inert to the solvent and which has low solubility in the solvent, the sparging being continued for a period of time sufficient to substantially eliminate gases of air from the same and to saturate the solvent with the sparging gas.

9. A method as in claim 8 in which the rate with which the sparging gas is supplied is reduced and then continued at a lower rate until said one solvent is supplied to the system.

* * * * *